(12) United States Patent
Simkins, Jr.

(10) Patent No.: US 8,479,588 B1
(45) Date of Patent: Jul. 9, 2013

(54) METHOD FOR CRACK AND FRACTURE MODELING IN DIRECTED SURFACES

(75) Inventor: Daniel C. Simkins, Jr., Wesley Chapel, FL (US)

(73) Assignee: University of South Florida, Tampa, FL (US)

(*) Notice: Subject to any disclaimer, the term of this patent is extended or adjusted under 35 U.S.C. 154(b) by 247 days.

(21) Appl. No.: 12/915,677

(22) Filed: Oct. 29, 2010

Related U.S. Application Data

(60) Provisional application No. 61/256,018, filed on Oct. 29, 2009.

(51) Int. Cl.
*G01N 19/08* (2006.01)

(52) U.S. Cl.
USPC .......................................................... 73/799

(58) Field of Classification Search
USPC .......................................................... 73/799
See application file for complete search history.

(56) References Cited

U.S. PATENT DOCUMENTS

| | | | |
|---|---|---|---|
| 7,467,070 B2 * | 12/2008 | Meyer et al. ...................... | 703/1 |
| 7,480,573 B2 * | 1/2009 | Toyosada .......................... | 702/34 |
| 7,505,885 B2 * | 3/2009 | Deobald et al. ................... | 703/7 |

OTHER PUBLICATIONS

Liu et al., Reproducing Kernel Particle Methods, International Journal for Numerical Methods in Fluids, 1995, vol. 20, pp. 1081-1106.
Simkins et al., Meshfree Simulations of Thermo-Mechanical Ductile Fracture, Comput. Mech., 2006, vol. 38, pp. 235-249.
Buchanan et al., Micromechanical Enhancement of the Macroscopic Strain State for Advanced Composite Materials, Composites Science and Technology, 2009, vol. 69, pp. 1974-1978.
Rabczuk et al., A Simple and Robust Three Dimensional Cracking Particle Method Without Enrichment, Computer Methods in Applied Mechanics and Engineering, 2010, pp. 1-42.

\* cited by examiner

*Primary Examiner* — Lisa Caputo
*Assistant Examiner* — Octavia D. Hollington
(74) *Attorney, Agent, or Firm* — Andriy Lytvyn; Jeremy Spier; Smith & Hopen, P.A.

(57) ABSTRACT

A method for three-dimensional crack propagation, morphology, and initiation suited to directed surfaces, or stacks of directed surfaces. An external damage measure and failure criteria can be incorporated, as well as a rule-based crack direction and morphology capability. This method is ideal for laminated composites. Further, the use of external damage and failure, and rule-based crack propagation, this method is ideal for multi-scale modeling and use in applications where knowledge and rules are necessary or desirable for guiding, driving, or influencing failure modes, directions, or other situations that are not directly incorporated into the governing mechanical equations.

8 Claims, 9 Drawing Sheets

| Quantity | Value | Quantity | Value |
|---|---|---|---|
| Length (m) | 2.540e-1 | $G_{12}$ (Pa) | 4.137e9 |
| Thickness (m) | 1.270e-2 | $G_{13}$ (Pa) | 4.137e9 |
| Height (m) | 5.080e-2 | $G_{23}$ (Pa) | 3.329e9 |
| $E_1$ (Pa) | 1.379e11 | $\alpha_1$ (K$^{-1}$) | 0.000e0 |
| $E_2$ (Pa) | 9.653e9 | $\alpha_2$ (K$^{-1}$) | 1.111e-5 |
| $E_3$ (Pa) | 9.653e9 | $\alpha_3$ (K$^{-1}$) | 1.111e-5 |
| $\nu_1$ | 3.300e-1 | $\Delta T$ (K) | -1.694e2 |
| $\nu_2$ | 3.300e-1 | | |
| $\nu_3$ | 4.500e-1 | | |

METHOD FOR CRACK AND FRACTURE MODELING IN DIRECTED SURFACES

CROSS REFERENCE TO RELATED APPLICATION

This application claims priority to U.S. provisional patent application No. 61/256,018, entitled "A METHOD FOR CRACK AND FRACTURE MODELING IN DIRECTED SURFACES," filed on Oct. 29, 2009, the contents of which are hereby incorporated by reference.

BACKGROUND OF THE INVENTION

1. Field of the Invention

This invention relates to a three dimensional crack and fracture morphology and propagation method for single and stacked directed surfaces that naturally incorporates external information.

2. Description of the Prior Art

A physical phenomenon, such as a fracture, fundamentally occurs in a discontinuous fashion. However, most methods for solving structural mechanics problems (e.g. the finite element method) are formulated to solve for continuous field variables. To model a crack in a continuum model requires embedding some model of discontinuity into the continuous formulation. Numerous approaches using this methodology have been introduced, such as X-FEM, cohesive cracks, element erosion, etc. These methods have achieved some degree of success. Purely discrete models, such as molecular dynamics (MD), can naturally evolve to open up discontinuities in a material. However, the number of molecules required for MD simulations capable of modeling practical engineering fracture problems is prohibitively large. Thus, there seems to be a place for a simple method to solve the continuum equations, but easily incorporate discontinuities.

The standard method of modeling composites is the continuum approach where the effect of the composite fibers is idealized as material properties of a linear elastic model. This is a form of the multiscale problem. The fibers themselves are too small a scale to be modeled explicitly and therefore this information is included in the model in the form of material properties. Even if the small scale of the fibers could be represented, the actual location in the matrix is knowledge that is difficult (if not impossible) to obtain with any reliable amount of certainty. The linear-elastic continuum approach works well for applications provided that the composite material properties are accurately determined. However, when failure is to be modeled, especially cracking, the information lost in the idealization of the fibers becomes critical. Cracking models based on continua will not predict the correct crack morphology due to the absence of actual fibers.

Moreover, for laminated composites, the fiber orientation has a profound effect on how cracks can propagate. In mesh-based analysis methods, the mesh orientation may influence the crack direction, but it may conflict with the physical requirements dictated by the fiber orientation.

Accordingly, what is needed is a method that explicitly models cracks and changing topology and is formulated to reduce or eliminate discretization choices from influencing the solution.

What is also needed is a method that naturally provides a mechanism for incorporating information that is not contained in the governing continuum equations to determine crack initiation and direction.

What is further needed is a method that returns physical knowledge to the model without the need to explicitly model fibers in the composite and enables the straightforward use of continuum mechanics to solve crack propagation problems in laminate fibrous composites which will model the physical behavior.

However, in view of the prior art considered as a whole at the time the present invention was made, it was not obvious to those of ordinary skill in the art how the limitations of the art could be overcome.

SUMMARY OF THE INVENTION

The long-standing but heretofore unfulfilled need for a method to solve the continuum equations that incorporates discontinuities is now met by a new, useful, and nonobvious invention.

The continuum body is modeled using a collection of interacting particles. Cracks are modeled by controlling which particles are allowed to interact through a visibility condition. The visibility condition uses a piece-wise surface object called a crack panel that provides a barrier to particle interaction, like an opaque window. For three-dimensional directed surfaces, the through-thickness is discretized with self-similar particle distributions. This allows the definition of a filament, an identifiable set of particles through the thickness of the surface with the direction of the filament parallel to the directed surface's normal. Cracks propagate from filament to filament and the crack tip always lies on a filament location.

The use of the filament concept allows the two-dimensional crack morphology and propagation method to be extended to three-dimensional directed surfaces. The method of crack propagation includes: (1) searching filaments in the vicinity of the current crack tip and assessing each filament for the value of the external damage measure; (2) choosing the filament with the highest damage, and if it meets a failure criteria, identify that filament as the next crack tip; (3) splitting each particle on the current fiber into two state preserving particles and inserting a crack panel from the current crack tip to the new crack tip separating the split particles; (4) updating the connectivity of the particles due to the new crack panel; and (5) repeating the method.

The above method is suitable for single directed surfaces. To extend the method to multiple stacked directed surfaces, the method of crack propagation further includes: (1) modeling each ply of the stacked surface as a single directed surface; (2) discretizing each ply in self-similar particle distributions; (3) identifying filaments in each ply and the filaments align at ply boundaries; (4) identifying particles as being either intra- or inter-ply; (5) treating intra-ply particles exactly as in the single surface case, whereby external rules for how to treat inter-ply particles can be used within the search performed to allow different modeling scenarios, including embedded general three-dimensional cracks, as well as laminated composites. Inter-ply particles, for example, can split in delamination, or in intra-ply facture, whereas intra-ply particles are restricted to intra-ply fracture only. Any set of rules can be developed and employed for the different particles, yielding many different crack propagation and morphology capabilities.

The keys to the method include: particle splitting in a state-preserving way, dynamic changing of the topology (particle connectivity) by use of the crack panels, and the ability in the search stage and computation of damage and failure criteria to accommodate any failure mechanism, including external rule-based models.

Moreover, the method allows for modeling of emergent cracks. To identify the location of crack initiation in an uncracked body, the external damage measure and failure criteria are applied to every filament in the body. Once a filament meets the criteria for failure, it is selected as a crack tip. Then a search is done (as in searching filaments in the vicinity of the current crack tip and assessing each filament for the value of the external damage measure described above) to find the next closest filament to failure. It is selected as another crack tip and a crack panel is inserted between the two filaments. The connectivity is then re-computed and the computation proceeds. Thus, a new emergent crack is inserted into the body.

BRIEF DESCRIPTION OF THE DRAWINGS

For a fuller understanding of the invention, reference should be made to the following detailed description, taken in connection with the accompanying drawings, in which:

FIG. 9 is a table showing material property values for beam problem. E, °, G, and a refers to elastic modulus, Poisson's ratio, shear modulus, and thermal expansion coefficient, respectively; the subscripts 1, 2, and 3 refer to the local orientation of the laminate where the 1 direction coincides with the fiber orientation.

DETAILED DESCRIPTION OF THE PREFERRED EMBODIMENT

Figure 1:
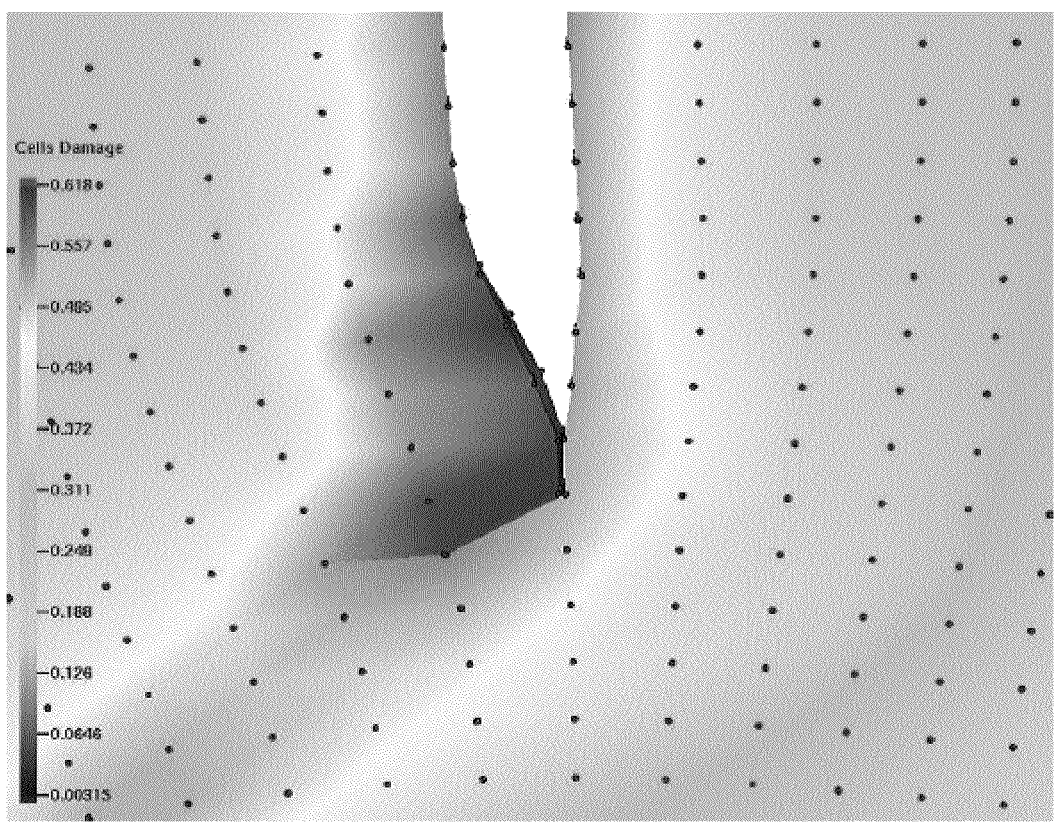
FIG. 1 is a close-up view of the crack tip and demonstrates propagation method.

The Reproducing Kernel Particle Method (RKPM) [1] provides a method to construct a function basis for use in Galerkin solutions to partial differential equations without using a mesh; instead, the RKPM method uses local and dynamic interactions between nodes (particles). Since a mesh is not required to form the function space, it can evolve dynamically; in particular, it can be adjusted as the material topology changes. The RKPM method constructs a local interpolation field centered at each node that is based on local interaction with neighboring nodes. By introducing a visibility condition during a calculation, one can selectively limit the interaction between nodes to effectively cut the material. A version applicable to two-dimensional problems was presented in [2].

The node splitting method uses information determined from either the constitutive model or other, possibly external, source, to determine when a node should be split. Based upon this damage measure, the crack propagation method automatically chooses crack direction and propagation. The ability to couple node splitting to a damage measure is immensely powerful. In fact, it can be viewed as a link between the structural mechanics equations and an externally (to the mechanics equations) determined quantity. There is no need for the external quantity to be continuous and its insertion into the simulation is done for each node—and is thus discontinuous. Proper selection of the external damage measure allows a researcher to incorporate information from knowledge bases, or detailed physics-based multi-scale calculations.

The crack morphology is simulated using RKPM in conjunction with a particle splitting method. The method models cracks in three-dimensional solids where the crack passes through the thickness of the solid. This is ideal for use in thin walled structures such as pressure cylinders and aircraft hulls. The crack is restricted to move only between particles. The interpolation field is dynamically altered by changes in particle topology due to this cracking by use of a visibility criterion. A crack will propagate when a threshold of material utilization is reached, moving in the direction of the neighboring particle with highest utilization.

While the cracking method will function with any failure discriminator, in this case we base failure for a laminated glassy polymer using the method as described in [2]. Here, a unique discriminant is described which reflects failure in the matrix due to distortional strain and failure in the fiber due to shearing strain.

The idealization of the fibers as material properties comes at the cost of accuracy. For added accuracy, prior to the calculation of material utilization, the states of strain are micro-mechanically enhanced using a technique detailed in [2]. While the modeling of composites as continua is a natural solution, there are residual strains induced by the fiber-matrix interface not captured by the linear elastic model. This enhancement technique corrects the strains, adding more physics to the approximated solution.

The particle splitting method used to model the crack propagation also suffers from the lack of explicitly modeled fibers. The morphology is only guided by the measure of material utilization; however, there are crack trajectories generated by this method that are unphysical. This method is concerned with detailing a technique for restoring lost information to the propagation method.

Figure 2:
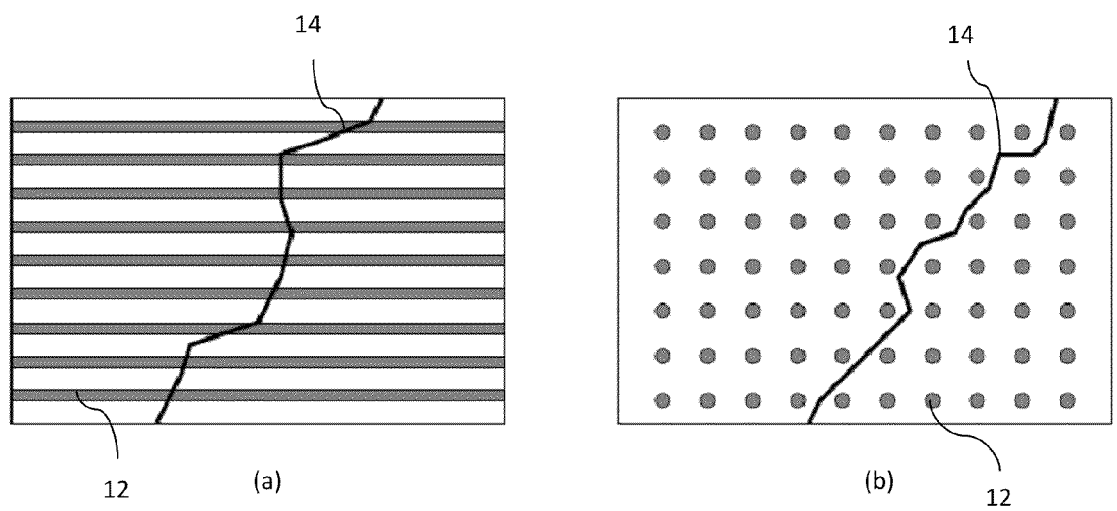
FIG. 2(a) is a schematic of a single-ply composite showing fibers in grey and matrix in white showing a restricted crack morphology.
FIG. 2(b) is a is a schematic of a single-ply composite showing fibers in grey and matrix in white and is permitted as no fibers are severed.

The method can be generalized as a list of criteria that limits the possible locations to which a crack may propagate. First, we restrict the cracking to be in the orientation of the fibers. Cracking against the fiber orientation requires that the fibers fail, which typically does not occur under normal loading. This situation can be seen in FIGS. 2(a) and (b). In FIG. 2(a), the fibers 12 are oriented from left to right and the crack 14 passes through them. This kind of morphology is restricted because it is unphysical. In FIG. 2(b), the fibers 12 are oriented into the page and the crack shown in the matrix only.

In a multi-layer laminate, cracking does not propagate from one laminate to another. Instead, delamination occurs when the crack reaches the interface. This is handled by limiting the meshfree particles to which a crack may propagate. Consider FIG. 3, where a portion of a 0°/90°/0° laminate composite is shown. The 0° plies are shaded and the fibers oriented left to right. The 90° ply is left white and its fibers are aligned coming in and out of the page. The small circles drawn represent the distribution of meshfree particles.

Figure 3:
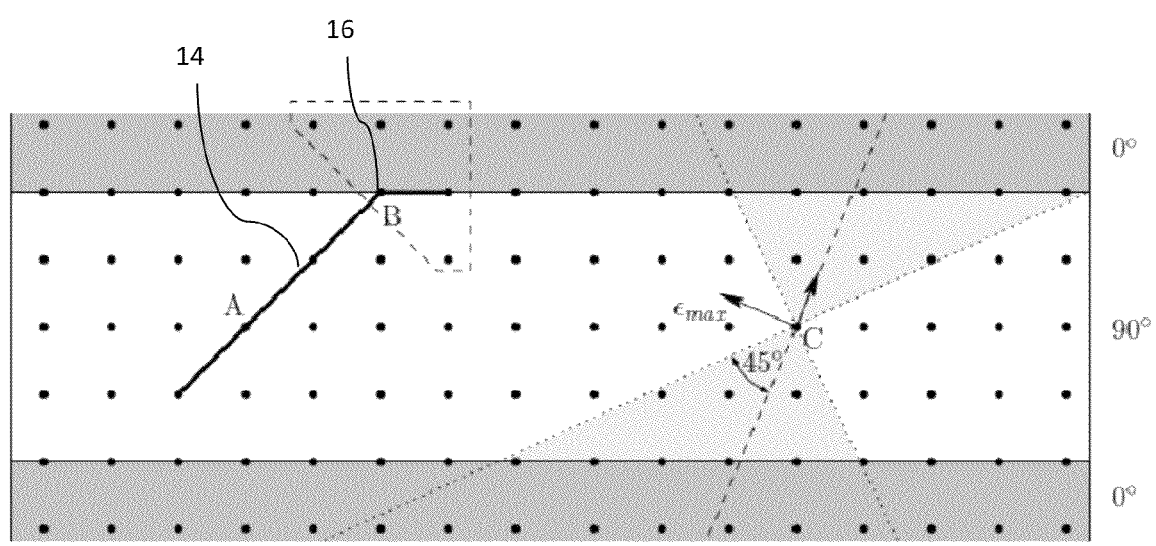
FIG. 3 is a portion of a 0°/90°/0° laminate composite.

Still referring to FIG. 3, the crack 14 is free to propagate in the lamina until it reaches the interface 16, represented here by a particle B. The normal cracking algorithm allows propagation to any neighboring particle in front of particle B. In this case, these candidate particles are indicated by a region defined by a dashed line. However, if at a laminate interface 16, the propagation cannot move into the next lamina, nor return into the original lamina. Instead, once a crack 14 reaches this interface 16, the crack 14 may only propagate in such a way as to cause delamination. This is consistent with what is physically seen in experiments.

When cracks initiate inside a lamina, a criteria also governs the subset of particles to which cracks may propagate. Consider a particle labeled C in FIG. 3, which represents the initiation of a crack. To determine candidate propagation particles, we use the following procedure:

1. Extract the state of strain in the plane normal to the fiber direction from the total strain tensor. For the 90°±ply in FIG. 3, this corresponds to the state of strain in the plane corresponding to that of the page.
2. Determine the maximum principle strain ($\epsilon$max) and accompanying direction. In FIG. 3, this direction is depicted as a vector originating at particle C and labeled, $\epsilon$max. This is observed to be the direction in which cracks open in the laminates.
3. The crack propagation direction is perpendicular to the maximum principle strain. Due to coarse granularity of the particle distribution, it is unlikely that a particle to which a crack may propagate exists in this direction. Candidate particles are chosen to lie within the 45° cone around this direction as well as in the current layer of the lamina. These particles are shown with light shading in FIG. 3.

These candidate particles are determined as a crack initiates, and maintained as it propagates. As the crack propagates and searches for new crack directions, particles which are not in the candidate subset determined when the crack initiated are ignored.

Figure 4:
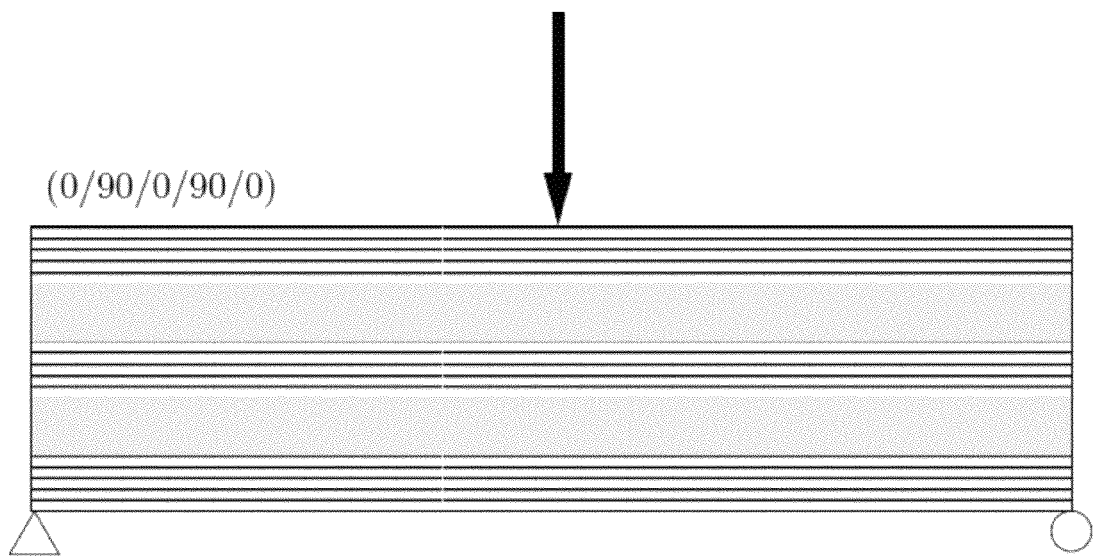
FIG. 4 is a schematic of the three-point bending problem.
Figure 5:
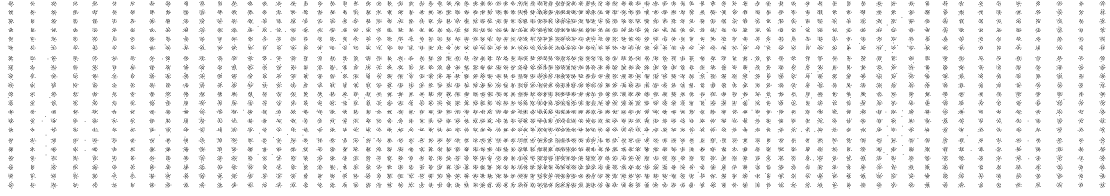
FIG. 5 is a particle distribution for beam problem (5733 particles), two-dimensional distribution shown with three particles through the thickness.

The efficacy of the method was tested on the following beam problem subjected to bending. The schematic for this problem can be seen in FIG. 4. There are five lamina shown in a 0°/90°/0°/90°/0° configuration. This beam was represented by a collection of particles in three-dimensional space shown in FIG. 5. The RKPM basis functions used reproduce a trilinear polynomial field and the window function selected was the radially based conical function, $$w(r)=(1-(r/\rho)^2))^2$$

Each of the laminae used were of the same material whose properties are summarized, as shown in FIG. 9. Note the thermal properties provided. A temperature difference is included which represents the change in temperature from the moment the lamina were manufactured until the cooled finished product. Since this laminate posses different thermal expansions in the fiber direction than orthogonal to the fiber direction, there are thermal strains that are present before loading occurs. These thermal strains were included in the simulation and computed as part of the initial state.

Figure 6:
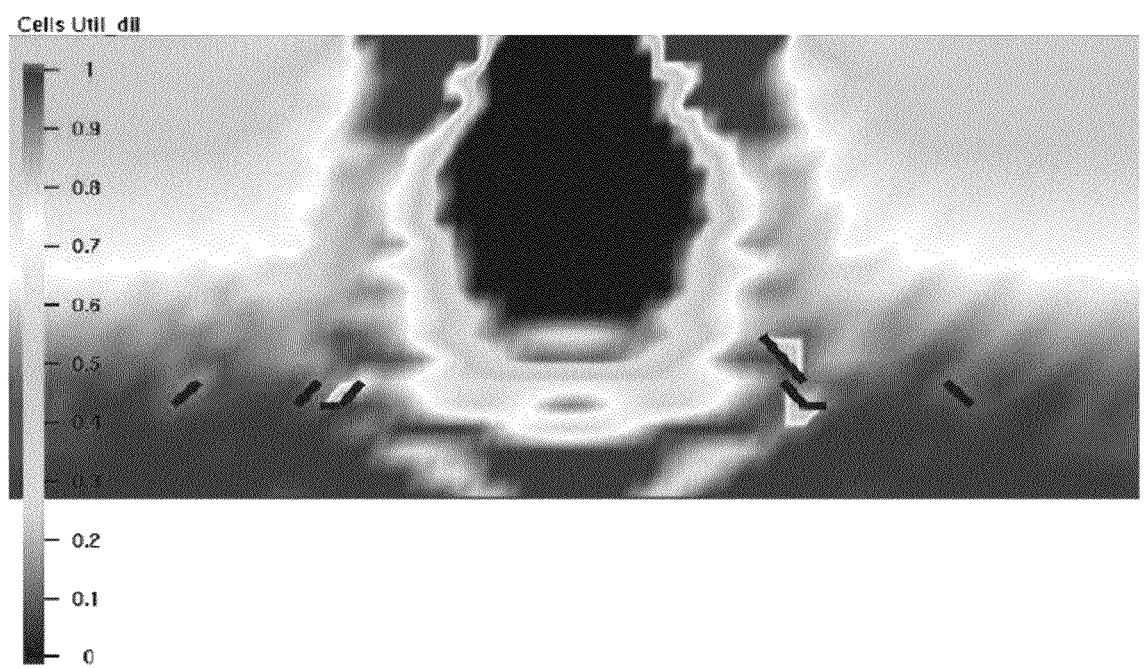
FIG. 6 is Material utilization based on dilatational strain.

In FIG. 6, an enlarged, central section of the beam is shown with values of the dilatation strain based material utilization shown interpolated between particles. The dark rectangles shown represent cracks that have started and begun to propagate. Note that these cracks have initiated in the 90° ply and are oriented in a manner consistent with the loading of the beam. The cracks nearest the center on both sides have initiated within the lamina and in two cases have begun to cause delamination.

The use of the model was successful in producing an analysis which correctly predicted the location and propagation of failure without the use preknowledge of where failure should occur. This in and of itself is a significant result. To accomplish this, a linear-elastic model was used with strain-based discriminators of failure. The states of strain were micromechanically enhanced to correct for the residual matrix-fiber strains present. Finally the meshfree crack propagation method was enhanced with physical knowledge, the result of which is a high fidelity solution.

Figure 7:
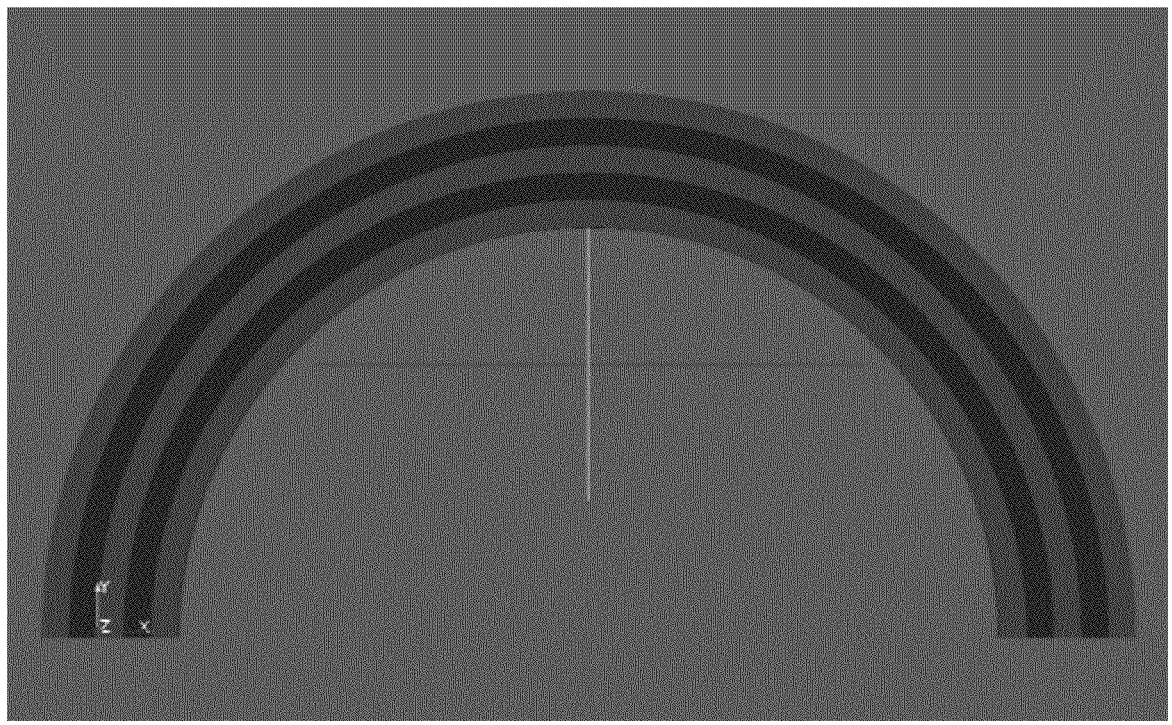
FIG. 7 is the undeformed configuration of the interlaminar tension curved beam with h 0°/90°/0°/90°/0° layup.
Figure 8:
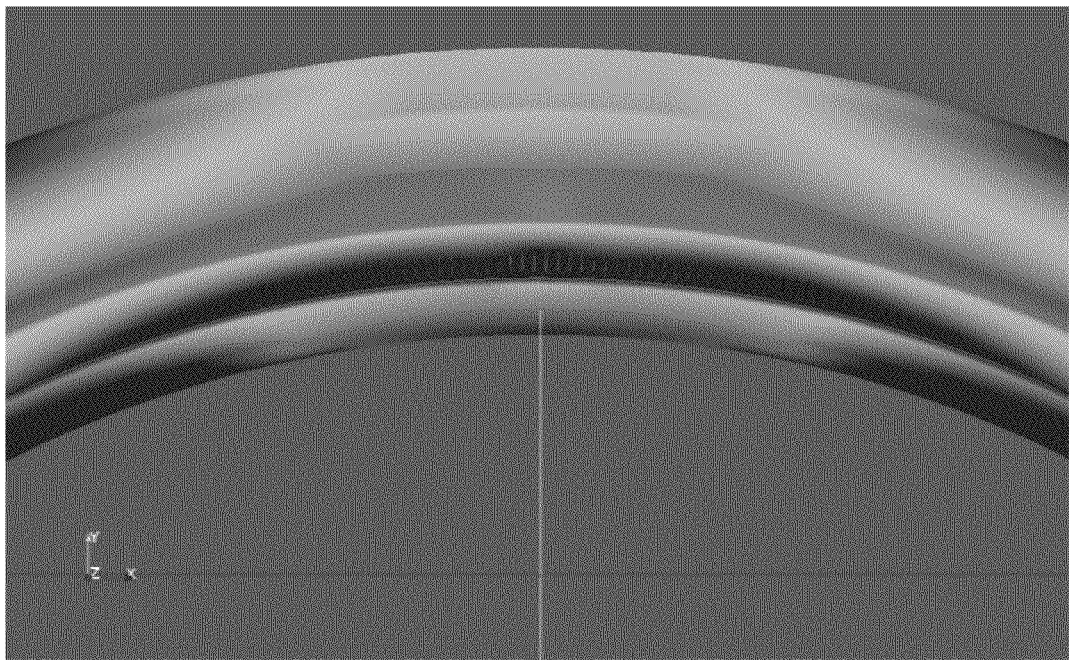
FIG. 8 is the resulting delamination and subsequent transverse cracking in inter-laminar tension failure of the curved beam.

The method was demonstrated on an inter-laminar tension failure problem for a cured beam. The undeformed shape and layup is depicted in FIG. 7. The bottoms of the beam are pulled apart resulting in the origination of delamination between the bottom two plies and subsequent transverse cracking of the interior ply after delamination, as shown in FIG. 8. Color contours represent the degree of material utilization.

REFERENCES

[1] W. K. Liu, S. Jun, and Y. F. Zhang. Reproducing kernel particle methods. *International Journal for Numerical Methods in Fluids*, 20:1081-1106, 1995.

[2] D. C. Simkins and S Li. Meshfree simulations of thermo-mechanical ductile fracture. *Computational Mechanics*, 38:235-249, 2006.

[3] David L. Buchanan, Jonathan H. Gosse, Jeffrey A. Wollschlager, Andrew Ritchey, R. Byron Pipes. Micromechanical enhancement of the macroscopic strain state for advanced composite materials. *Composites Science and Technology*, in press, 2009.

It will thus be seen that the objects set forth above, and those made apparent from the foregoing disclosure, are efficiently attained. Since certain changes may be made in the above construction without departing from the scope of the invention, it is intended that all matters contained in the foregoing disclosure or shown in the accompanying drawings shall be interpreted as illustrative and not in a limiting sense.

It is also to be understood that the following claims are intended to cover all of the generic and specific features of the invention herein disclosed, and all statements of the scope of the invention that, as a matter of language, might be said to fall therebetween.

What is claimed is:

1. A three dimensional crack and fracture morphology and propagation method for single directed surfaces, comprising the steps of:

defining a collection of interacting particles;

determining which particles are allowed to interact through a visibility condition, said visibility condition using a piece-wise surface object called a crack panel as a barrier to particle interaction;

defining filaments by discretizing a through-thickness with self-similar particle distributions, the filament being an identifiable set of particles through the thickness of a directed surface where the direction of the filament is parallel to a normal of the directed surface;

identifying a current crack tip, the crack tip being located on a filament and propagating between adjacent filaments;

searching filaments in a vicinity of the current crack tip and assessing each filament for a value of an external damage measure;

choosing a filament with the highest damage, and if said filament meets a failure criteria, identifying said filament as the next crack tip;

splitting each particle on the current filament into two state preserving particles and inserting a crack panel from the current crack tip to the new crack tip separating the split particles; and updating the connectivity of the particles due to the new crack panel.

2. A three dimensional crack and fracture morphology and propagation method of claim 1, further comprising the step of extracting a state of strain in a plane normal to fiber direction from a total strain tensor.

3. A three dimensional crack and fracture morphology and propagation method of claim 2, further comprising the step of micro-mechanically enhancing the state of strain.

4. A three dimensional crack and fracture morphology and propagation method of claim 1, further comprising the step of restricting crack porpagation to be in orientation of fibers.

5. A three dimensional crack and fracture morphology and propagation method of claim 1, further comprising the step of determining a maximum principle strain and direction thereof, wherein crack propagation direction is perpendicular to the maximum principle strain.

6. A three dimensional crack and fracture morphology and propagation method of claim 1, further comprising the step of limiting candidate particles for the next crack tip to lie within a 45° cone around the direction of crack propagation and originating at the current crack tip.

7. A three dimensional crack and fracture morphology and propagation method for multiple stacked directed surfaces, comprising the steps of:
    defining a collection of interacting particles;
    determining which particles are allowed to interact through a visibility condition, said visibility condition using a piece-wise surface object called a crack panel as a barrier to particle interaction;
    defining filaments by discretizing the through-thickness with self-similar particle distributions, the filament being an identifiable set of particles through the thickness of a directed surface where the direction of the filament is parallel to a normal of the directed surface;
    identifying a current crack tip, the crack tip being located on a filament and propagating between adjacent filaments;
    searching filaments in a vicinity of the current crack tip and assessing each filament for a value of an external damage measure;
    choosing a filament with the highest damage, and if said filament meets a failure criteria, identifying said filament as the next crack tip;
    splitting each particle on the current filament into two state preserving particles and inserting a crack panel from the current crack tip to the new crack tip separating the split particles;
    updating the connectivity of the particles due to the new crack panel;
    modeling each ply of the stacked surface as a single directed surface;
    discretizing each ply in self-similar particle distributions;
    identifying filaments in each ply, but also the filaments align at ply boundaries;
    identifying particles as being either intra- or inter-ply;
    treating intra-ply particles exactly as in the single surface case; and
    whereby external rules for how to treat inter-ply particles can be used within the search performed to allow different modeling scenarios, including embedded general three-dimensional cracks, as well as laminated composites.

8. A three dimensional crack and fracture morphology and propagation method for modeling emergent cracks, comprising the steps of:
    applying an external damage measure and failure criteria to every filament in a body, the filament being an identifiable set of particles through the thickness of a directed surface where the direction of the filament is parallel to a normal of the directed surface;
    selecting a crack tip once a filament meets the criteria for failure, said crack tip being located on said filament and propagating between adjacent filaments;
    searching filaments in a vicinity of said current crack tip and assessing each filament for a value of an external damage measure;
    choosing a filament with the highest damage and identifying said filament as the next crack tip;
    inserting a crack panel from the current crack tip to the new crack tip; and
    updating the connectivity of the particles due to the new crack panel.

* * * * *